United States Patent [19]
Peet et al.

[11] Patent Number: 6,034,241
[45] Date of Patent: Mar. 7, 2000

[54] PROCESS FOR CONVERTING HYDROXY HETEROAROMATICS TO ARYLAMINES

[75] Inventors: Norton P. Peet, Neshanic Station, N.J.; John J. Weidner, Creve Coeur, Mo.

[73] Assignee: Hoechst Marion Roussel Inc., Bridgewater, N.J.

[21] Appl. No.: 08/978,567

[22] Filed: Nov. 26, 1997

Related U.S. Application Data

[60] Provisional application No. 60/069,321, Nov. 27, 1996.

[51] Int. Cl.$^7$ ......................... C07D 215/38; C07D 211/72
[52] U.S. Cl. ............................................. 546/159; 546/311
[58] Field of Search ...................................... 546/159, 311

[56] References Cited

FOREIGN PATENT DOCUMENTS 9734916  9/1997  WIPO.

OTHER PUBLICATIONS

Coutts et al., J. Chem. Soc. Perkin Trans. 1, pp. 767–771 (1990).
Bayles et al., Synthesis, (1977), pp. 31–33.
Bayles, et al., Synthesis 31:33–34 (1977).
Weidner et al., Amer. Chem. Soc. Division of Org. Chem., 211th ACS National Meeting, New Orleans, LA, Mar. 24–28, 1996, #054.
Alford et al., J. Chem. Soc. pp. 3009–3017 (1952).
von A. Stoll et al., Helvetica Chimica Acta., 36(140):1125–1137 (1953).
Goheen et al., J. Org. Chem., 23:891–893 (1958).
Belser et al., Tetrahedron, 52(8):2937–2944 (1996).
The Merck Index of Chemicals and Drugs, pp. 50 and 60, 1960.

*Primary Examiner*—D. Margaret Seaman
*Attorney, Agent, or Firm*—T. Helen Payne

[57] ABSTRACT

A process of converting a hydroxy heteroaromatic compound to an arylamine, comprising the steps of:
  (1) treating a salt of a hydroxy heteroaromatic compound with an alkylating agent; and
  (2) treating the reaction mixture with a Smiles solvent system and raising the temperature of the reaction mixture; and A compound made according to the above process.

26 Claims, No Drawings

PROCESS FOR CONVERTING HYDROXY HETEROAROMATICS TO ARYLAMINES

This application claims the benefit of provisional application Serial No. 60/069,321, filed Nov. 27, 1996.

The present invention refers to an alternative synthesis to the Bucherer reaction, where a hydroxy group on a nitrogen-containing heteroaromatic ring is converted into an amine. This alternative synthesis involves a modified Smiles rearrangement without purifying intermediates and avoids the undesirable reaction conditions required for the Bucherer reaction.

BACKGROUND OF INVENTION

A Smiles rearrangement describes a pattern of reactions involving intramolecular nucleophilic aromatic substitution which results in the replacement of one heteroatom to another on an aromatic ring and works with a variety of heteroatoms, including oxygen, sulfur and nitrogen. A Smiles rearrangement of phenols, including fused-ring heterocyclic phenols, into corresponding anilines is described by I. G. C. Coutts and M. R. Southcott in *J. Chem. Soc. Perkin Trans. I*, 1990;767–771, where the hydroxy group on an aromatic ring, optionally fused into a larger ring system, is replaced with an amino group. However, Coutts and Southcott describe the synthesis as a distinct three-step process, with the purification of each intermediate. The first step is a conversion of the alcohol to a 2-aryloxyacetamide. The second step is the actual Smiles rearrangement of the aryloxyacetamide to a 2-hydroxy-N-arylacetamide. Finally, the 2-hydroxy-N-arylacetamide is hydrolyzed to the corresponding aromatic amine. The known Smiles rearrangements of aromatic amides involves purification of the 2-aryloxyacetamide intermediates.

A simplified Smiles rearrangement which avoided purification of the 2-aryloxyacetamide intermediates was recently described in J. J. Weidner, P. M. Weintraub, and N. P. Peet, 209th National Meeting of the American Chemical Society, Mar. 24–29th, 1996, New Orleans, La., ORGN 54. This process provided a concise route to 3-aminoestratrienes and is exemplified by conversion of estrone to the corresponding amino derivative by a Smiles rearrangement of a 2-aryloxyacetamide to a 2-hydroxy-N-arylacetamide.

The Bucherer reaction is a method of direct conversion of hydroxypyridines and related heterocycles to their amino derivatives. The Bucherer reaction is a well-documented method for direct conversion of hydroxynaphthalenes, hydroxyquinolines, and related heterocycles to their corresponding amines. This reaction is described in Jerry March, Advanced Organic Chemistry: Reactions, Mechanisms and Structure, 3rd edition, John Wiley and Sons, New York, 1985, p. 591–592, incorporated by reference herein. Numerous literature references exemplify the utility of the Bucherer reaction. For example, E. C. Hurdis, *J. Org. Chem.*, 1958, 23; 891–89, describes conversion of 8-hydroxyquinoline to 8-aminoquinoline in high yield by application of this reaction. In a similar manner, a series of substituted 8-aminoquinolines was recently synthesized as starting materials for the preparation of substituted 1,10-phenanthrolines. P. Belser, S. Bernhard and U. Guerig, *Tetrahedron*, 1996, 52(8); 2937–2944. 8-Aminocinnoline has been obtained from 8-hydroxycinnoline by this methodology. E. J. Alford, H. Irving, H. S. Marsh and K Schofield, *J. Chem. Soc.*, 1952; 3009–3017. A series of derivatives of lysergic acid was synthesized using a similar protocol. A. Stoll, T. Petrzilka *Helv. Chim. Acta*, 1953, 36; 1125–1137.

Despite the demonstrated utility of the Bucherer method, there are several serious drawbacks. It requires the use of corrosive liquid ammonia in sealed vessels at high temperatures. Along with these potential dangers, the scale is limited without the use of large specialized equipment. Substrates are limited to those resistant to high temperatures and basic conditions. Reactions may also take up to a week to go to completion.

Therefore, there is a need for a general method for converting hydroxypyridines to their corresponding amino derivatives which is applicable to a broad range of hydroxypyridines, does not require the use of liquid ammonia or sealed vessels, is easy to scale up, requires few steps and produces good yields.

SUMMARY OF THE INVENTION

The present invention is an alternative to the Bucherer method of converting hydroxypyridines to their corresponding amino derivatives. The present process is a modified alkylation, Smiles rearrangement and subsequent spontaneous hydrolysis to form the corresponding amine. Avoidance of purification steps is significant in terms of minimizing time, cost and resources necessary during the synthesis of aminopyridines and yet provide good overall yields.

The present invention is a process of converting a hydroxy heteroaromatic compound into an arylamine, comprising the steps of:

(1) treating a salt of a hydroxy heteroaromatic compound with an alkylating agent; and (2) treating the reaction mixture with a Smiles solvent system and raising the temperature of the reaction mixture.

DETAILED DESCRIPTION OF THE INVENTION

The present invention is an alternative to the Bucherer reaction and provides a process of effecting an alkylation, Smiles rearrangement and subsequent hydrolysis of a hydroxy heteroaromatic compound to an arylamine, without purifying intermediates. Optionally, a salt of the hydroxy heteroaromatic is formed in the presence of an alkylating solvent system, to which an alkylating agent is added. A Smiles solvent system is added to the reaction mixture containing the 2-aryloxyacetamide intermediate and the reaction mixture is heated to effect the Smiles rearrangement and form the acylated arylamine intermediate. Finally, the acylated arylamine intermediate hydrolyzes to the corresponding heterocyclic aromatic amine.

Suitable hydroxy heteroaromatic compounds for the present reaction are well-known to those skilled in the art. Preferred hydroxy heteroaromatic compounds include nitrogen-containing aromatic rings, such as N-substituted pyrroles, pyridines, N-substituted indoles, quinolines, isoquinolines, carbazoles, and acridines optionally substituted with one or more substituents. Partially and fully aromatic hydroxy heteroaromatic compounds may be used herein. However, when a partially unsaturated hydroxy heteroaromatic compound is used, the hydroxy group must be on an aromatic ring. The hydroxy heteroaromatic compound may be optionally substituted with either one or more electron-donating or one or more electron-withdrawing groups. However, the nitrogen-containing aromatic ring is preferably unsubstituted or substituted with electron-withdrawing groups. Preferred hydroxy heteroaromatic compounds are substituted at the meta and para positions. When electron-donating groups are substituted on the hydroxy heteroaromaticsystem, it is preferred that they are distal from the hydroxy substituent and not on the ring bearing the hydroxy group in a polycyclic compound.

Preferred electron-withdrawing groups include $NR_1R_2R_3^+$ (quaternary ammonium salts) where $R_1$, $R_2$ and $R_3$ are independently H, $C_{1-6}$ alkyl, $-NO_2$, $-CN$, $-SO_3H$, $-COOH$, CHO, $COR_4$, where $R_4$ is $C_{1-6}$ alkyl or $C_{1-6}$ alkoxy, and X, where X is a halogen selected from Cl, Br, I, F.

Preferred electron-donating groups include $-NH_2$, $-OH$, $-OCH_3$, $-NHCOCH_3$, $C_6H_5$, $-C_{1-6}$ alkyl and $-C_{1-6}$ alkoxy.

As used herein, the term "alkyl" means a carbon chain of one to six carbons, which may contain one or more double or triple bonds and are straight or branched, and optionally substituted with one or more halogen. Included within the term alkyl are methyl, ethyl, propyl, isopropyl, butyl, isobutyl, tert-butyl, cis-2-butene, trans-2-butene, hexyl, heptyl, and the like.

As used herein, the term "alkyloxy" means a carbon chain of one to six carbons containing an oxygen, which may contain one or more double or triple bonds, are straight or branched, and are optionally substituted with one or more halogen. Included within the term alkyloxy are methoxy, ethoxy, propoxy, isopropoxy, butoxy, isobutoxy, hexyloxy, heptoxy, and the like.

As used herein, the term "halogen" includes Cl, Br, I, F.

Preferred hydroxy aromatics are compounds of the formula indicated in Figures 1 through 4:

Figure 1
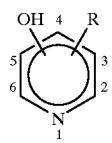

Figure 2
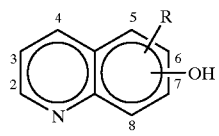

Figure 3
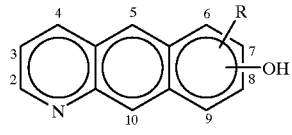

Figure 4
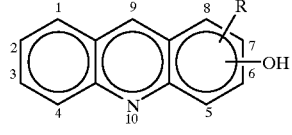

where R optionally represents from one to eight substituents independently selected from electron-withdrawing and electron-donating groups. Hydroxy aromatics may be simple hydroxy aromatics having a single aromatic ring, such as hydroxypyridines and substituted hydroxypyridines. Complex hydroxy aromatics may also be used in the present invention, where R groups may be combined to form multiple carbon fused ring structures of varying degrees of saturation, or where ring structures are attached as substituents. Suitable complex ring structures include fully aromatic complex ring structures such as pyridines, isoquinolines, quinolines, acridines, and the like, as well as their partially and fully saturated counterparts, such as tetrahydroisoquinolines, tetrahydroquinolines, tetrahydroacridines, and the like.

In complex ring structures, the carbon atoms in the rings other than those in the ring bearing the hydroxy group are optionally substituted with a wide variety of substituents known to those in the art, including $NH_2$, $NO_2$, SH, $SO_3H$, $CO_2H$, CN, halogens, thioethers, alkyl, alkoxy groups and other functional groups such as carbamates, ethers, amides, and esters.

Additional preferred hydroxy aromatic compounds which may be utilized as starting materials according to the present method include nicotine derivatives of the following general formula, Figure 5:

Figure 5
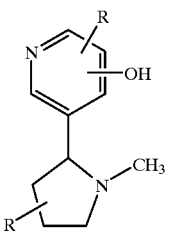

where the heteroaromatic ring contains at least one hydroxy group, and is additionally substituted with one to three independently selected R groups, as defined above. Additional modifications may be made to the heteropentane ring, whereby the ring is additionally substituted with one to four independently selected R groups, as defined above.

The salt of the hydroxy heteroaromatic compound may be formed according to methods well-known in the art. Preferably, the salt of the hydroxy heteroaromatic compound is formed in the presence of an alkylating solvent system, to which an alkylating agent is added.

The alkylating agent serves as a donor of a substituent capable of undergoing intramolecular nucleophilic substitution, or the Smiles rearrangement. Alkylating agents useful in the present invention are well known to those of ordinary skill in the art. Generally, suitable alkylating agents are comprised of an amide and halogen functional group separated by one carbon atom of the following general formula:

$$(R')(R'')(X)-C-C-(O)-NH_2$$

wherein X is a leaving group. Suitable leaving groups include halogens and OR, where R is p-toluenesulfonyl or methylsulfonyl. A preferred leaving group is selected from bromine, chlorine and iodine. An especially preferred leaving group is bromine.

R' and R" of the alkylating agent are independently H or $C_{1-6}$ alkyl, straight or branched chain. It is preferred that when one of R' or R" is hydrogen, the other is a larger alkyl such as isopropyl, sec-butyl or tert-butyl or equivalent pentyl or hexyl groups. It is especially preferred that when one of R' or R" is hydrogen, the other is tert-butyl. $C_{1-6}$ alkyl is a straight and branched one to six carbon group including methyl, ethyl, propyl, isopropyl, n-butyl, sec-butyl, tert-butyl, pentyl and hexyl.

A preferred alkylating agent is where X is a halogen and R' and R" is $C_{1-4}$ alkyl. An especially preferred alkylating agent is where X is bromine and at least one of R' and R" is methyl or ethyl. Preferred alkylating agents are secondary haloalkylamides and, most preferred are tertiary haloalkylamides, with 2-bromo-2-methylpropanamide and 2-bromo-2-ethylbutanamide being especially preferred.

The alkylating solvent system generally comprises a strong base, an ethereal solvent and a large alkaline metal cation.

A strong base is capable of extracting the alcoholic proton of the hydroxy aromatic. A single strong base may be used, or a combination of two or more strong bases may be used. Suitable strong bases include sodium hydride, potassium hydride, lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium, and mixtures thereof. The hydride bases are preferred, such as sodium hydride, lithium hydride, potassium hydride and mixtures thereof. Sodium hydride is especially preferred.

An ethereal solvent is used to solvate the reaction components, including the alkylating agent and large alkaline metal cation. The ethereal solvent should be polar and non-nucleophilic. Suitable ethereal solvents include 1,4-dioxane, 1,3-dioxane, tetrahydrofuran (THF), dimethoxyethane (DME), 2-methoxyethyl ether, propyl ether, isopropyl ether, n-butyl ether, sec-butyl ether, tert-butyl ether, n-butylmethyl ether, tert-butylmethyl ether, n-butylethyl ether, sec-butylethyl ether, tert-butylethyl ether, n-butylpropyl ether, sec-butylpropyl ether, tert-butylpropyl ether and mixtures thereof. Preferred ethereal solvents have relatively low boiling points. 1,4-Dioxane and 1,3-dioxane are preferred. 1,4-Dioxane is especially preferred.

A large alkaline metal cation is believed to function as an electron transfer facilitator. More specifically, the large metal cation is thought to promote radical alkylation reactions. Inorganic cesium compounds are preferred. Suitable examples of large alkaline metal cations include cesium carbonate ($Cs_2CO_3$), cesium acetate ($CsCO_2CH_3$), cesium bicarbonate ($CsHCO_3$), cesium bromide (CsBr), cesium chloride (CsCl), cesium fluoride (CsF), cesium iodide (CsI). Cesium carbonate is preferred.

A Smiles solvent system is added to the reaction mixture to promote the Smiles rearrangement. The Smiles solvent system is designed to solvate the reagents, act as an anion-coordinating agent by promoting and/or stabilizing the anionic form of the 2-aryloxyacetamide intermediate and to coordinate or make the 2-aryloxyacetamide intermediate a stronger nucleophile, through conversion into an anion, and thus facilitating a Smiles rearrangement.

A Smiles solvent system is a combination of amide solvent, an anion-coordinating agent and a strong base. Preferably, there are at least molar equivalents of the anion-coordinating agent to alkaline metal cation.

The Smiles solvent system may be premixed or each component added sequentially to the reaction mixture in any order.

A strong base is capable of extracting the amide proton of the 2-aryloxyacetamide intermediate. A single strong base or a combination of two or more strong bases may be used in the present invention. Suitable strong bases include sodium hydride, potassium hydride, lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium or mixtures thereof. The hydride bases are preferred, such as sodium hydride, lithium hydride and potassium hydride. Sodium hydride is especially preferred. The strong base may be the same strong base used as the strong base for alkylation.

The amide solvent is preferably 1-methyl-2-pyrrolidinone (NMP), dimethylformamide (DMF), dimethylacetamide (DMA) or mixtures thereof. NMP is the preferred amide solvent.

The anion-coordinating agent may be N,N'-dimethyl-N,N'-propyleneurea; also known as 1,3-dimethyltetrahydropyrimidin-2(1H)-one (DMPU) or hexamethylphosphoric triamide (HMPA) or a combination thereof. DMPU is the preferred anion-coordinating agent.

The volume ratio of amide solvent to anion-coordinating agent is optionally from about 1:1 to about 40:1. Preferably, the ratio of amide solvent to anion-coordinating agent is from about 5:1 to about 15:1. The ratio of amide solvent to anion-coordinating agent is especially preferred to be between about 7:1 to about 12:1. The most preferred ratio of amide solvent to anion-coordinating agent is about 10:1.

The salt of the hydroxy aromatic is formed by reacting a hydroxy aromatic in the presence of an alkylating solvent system. The reaction mixture is optionally stirred for a period sufficient to form a salt of the hydroxy aromatic. Preferably, when sodium hydride is used in the alkylating solvent system, evolution of hydrogen gas continues until the formation of the hydroxy aromatic salt is substantially complete. Preferably, the reaction mixture is heated during the formation of the salt. Higher temperatures generally require shorter reaction time for the formation of the salt and lower temperatures generally require longer reaction time.

An alkylating agent is added to the reaction mixture after formation of the hydroxy aromatic salt. Preferably, the reaction mixture is stirred at reflux until the alkylation is substantially complete. Reaction progress of the alkylation may be monitored by known techniques, including thin-layer chromatography (TLC), gas chromatography (GC) or high performance liquid chromatography (HPLC). TLC is preferred. After alkylation, a Smiles solvent system, preferably a combination of amide solvent, anion-coordinating agent and strong base, is added to the reaction mixture.

The temperature of the reaction mixture is raised to a temperature sufficient to effect the Smiles rearrangement. Faster reaction time is expected with higher temperatures and longer reaction time is expected with lower temperatures. Preferred reaction temperature is between about 65° C. to about 250° C., preferably between about 125° C. to 200° C. A more preferred reaction temperature is between about 125° C. to about 175° C. The most preferred reaction temperature is about 150° C. The reaction mixture is optionally stirred during the Smiles rearrangement.

Reaction progress of the Smiles rearrangement is optionally monitored by any known technique, for example, thin-layer chromatography (TLC), gas chromatography (GC), high performance liquid chromatography (HPLC). TLC is preferred. Upon completion of the Smiles rearrangement, the heterocyclic arylamine product is purified by known methods.

Compounds which may be synthesized by the present process include the following examples, which are not intended to be limiting but intended to illustrate the utility of the process herein.

EXAMPLE 1

8-hydroxyquinoline

Preparation of 8-aminoquinoline

To a solution of 8-hydroxyquinoline (537 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), eluting with 30:70:1 EtOAc/hexane/$NEt_3$ to obtain 8-aminoquinoline as an off-white solid (220 mg, 1.53 mmol, 41.3% yield).: mp 65–67° C. (lit. 62.5–64° C., Dewar, M. J. S. et. al., Journal of the Chemical Society, 1956, 2556 and 62.5–64° C., Richardson, A. et. al., Journal of Organic Chemistry, 1960, 25, 1138); $^1$H NMR (300 MHz, $CDCl_3$) δ8.76 (dd, 1 H, J=4.23, 1.75 Hz), 8.06 (dd, 1 H, J=8.20, 1.96), 7.37–7.30 (om's, 2 H), 7.15 (dd, 1 H, J=8.01, 1.30), 6.92 (dd, 1 H, J=7.51, 1.42), 4.98 (br s, 2 H, N—$H_2$); MS (EI) 144; Analysis: Calculated C 74.98, H 5.59, N 19.43; Found C 74.88, H 5.67, N 19.26.

EXAMPLE 2

4-hydroxyacridine

Preparation of 4-aminoacridine

To a solution of 4-hydroxyacridine (722 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), eluting with 1:9 then 3:7 EtOAc/hexane to obtain 4-aminoacridine as a brown solid (130 mg, 0.67 mmol, 18.1% yield).: mp 98–100° C. (lit 105–106° C., Albert, A. et. al., Chemistry and Industry (London), 1941, 60, 122T); $^1$H NMR (300 MHz, $CDCl_3$) δ8.66 (s, 1 H), 8.23–8.19 (m, 1 H), 7.98–7.95 (m, 1 H), 7.74–7.69 (m, 1 H), 7.53–7.48 (m, 1 H), 7.34 (d, 1 H, J=1.72 Hz), 6.94 (dd, 1 H, J=3.32 Hz), 5.23 (br s, 2 H, N—$H_2$); MS (CI/$NH_3$) 195; IR 3377 (NH).

Another fraction (90 mg of material) contained the rearrangement product by NMR, but the MS showed only m/z 113. The starting 4-hydroxyacridine was also recovered (90 mg, 12.4%).

EXAMPLE 3

8-hydroxyquinaldine

Preparation of 2-hydroxy-N-(8-quinaldinyl)-2-methylpropionamide

To a solution of 8-hydroxyquinaldine (722 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (50 mL), dried ($Na_2SO_4$), and concentrated to about 3 g of material. The brown oil, the rearrangement product, was chromatographed on silica (200 mL, 4 cm diam. column), eluting with 3:7 EtOAc/hexane to obtain the product as an off-white solid (610 mg, 2.50 mmol, 67.6% yield).: mp 143–144° C.: $^1$H NMR (300 MHz, $CDCl_3$) δ10.99 (br s, 1 H, N—H), 8.76–8.73 (m, 1 H), 8.03 (d, 1 H, J=8.26), 7.48–7.45 (om's, 2 H), 7.32 (d, 1 H, J=9.21), 2.80 (br s, 1 H, O—H), 2.75 (s, 3 H, Ar—$CH_3$), 1.62 (s, 6 H, C($CH_3$)$_2$); $^{13}$C NMR (75 MHz, $CDCl_3$) δ174.9, 157.4, 138.2, 136.3, 133.5, 126.2, 126.1, 122.4, 121.6, 116.3, 74.2, 28.1, 25.4; MS (CI/$NH_3$) 245; Analysis: Calculated C 68.83, H 6.60, N 11.47; Found C 68.78, H 6.56, N 11.37.

EXAMPLE 4

5-hydroxyquinoline

Preparation of 5-aminoquinoline

To a solution of 5-hydroxyquinoline (537 mg, 3.70 mmol) in dioxane (20 mL) was added NaH (Aldrich, dry, 300 mg, 12.2 mmol) and $Cs_2CO_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried ($Na_2SO_4$), and concentrated to about 3 g of material. The brown oil was chromatographed on silica (200 mL, 4 cm diam. column), eluting with 7:3 EtOAc/hexane to obtain 5-aminoquinoline as a brown solid (90 mg, 0.62 mmol, 16.8% yield).: mp 98–100° C. (lit. 108–109° C., Akita, Y., et. al., Synthesis, 1977, 792); $^1$H NMR (300 MHz, $CDCl_3$) δ8.89 (dd, 1 H, J=4.13, 2.06 Hz), 8.18 (dd, 1 H, J=8.49, 0.93), 7.60–7.48 (om's, 2 H), 7.35 (dd, 1 H, J=8.56, 4.26), 6.83 (dd, 1 H, J=7.13, 1.31), 4.21 (br s, 2 H, N—$H_2$); $^{13}$C NMR (75 MHz, $CDCl_3$) δ150.2, 149.1, 142.2, 130.0, 129.5, 120.1, 119.6, 118.7, 110.0; MS (CI/$CH_4$) 145.

The rearrangement product was also isolated from the column as a brown solid (480 mg, 2.08 mmol, 56.2% yield): mp 177–179° C.; $^1$H NMR (300 MHz, $CDCl_3$) δ9.37 (br s, 1H, N—H), 8.90 (dd, 1 H, J=4.26, 1.58 Hz), 8.21 (d, 1 H, J=8.22), 8.09 (d, 1 H, J=7.80 Hz), 7.96 (d, 1 H, J=8.66 Hz) 7.70 (apparent t, 1 H, J=8.06), 4.01 (br s, O—H), 1.63 (s, 6 H, C($CH_3$)$_2$) $^{13}$C NMR (75 MHz, $CDCl_3$) δ175.3, 150.1, 148.4, 132.3, 129.55, 129.46, 122.1, 120.9, 120.0, 47.8, 27.9; MS (CI/$CH_4$) 231: IR (KBr pellet) 1649 (CO), 3371 (OH).

EXAMPLE 5

6-hydroxyquinoline

Preparation of 6-aminoquinoline

To a solution of 6-hydroxyquinoline (537 mg, 3.70 mmol) in dioxane (20 mL) was added NaH (Aldrich, dry, 300 mg, 12.2 mmol) and Cs$_2$CO$_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried (Na$_2$SO$_4$), and concentrated to about 3 g of material. The brown oil was distilled by Kugelrohr to remove residual NMP and DMPU, then chromatographed on silica (200 mL, 4 cm diam. column), eluting with 70:30:1 EtOAc/hexane/NEt$_3$ to obtain 6-aminoquinoline as a brown solid (210 mg, 1.45 mmol, 39.2% yield).: mp 111–113° C. (lit. 116° C., Sykes, W. O., Journal of the Chemical Society, 1956, 3087); $^1$H NMR (300 MHz, CDCl$_3$) δ8.66 (dd, 1 H, J=4.27, 1.63 Hz), 7.93–7.87 (m, 2 H), 7.26 (dd, 1 H, J=8.24, 4.23 Hz), 7.16 (dd, 1 H, J=9.05, 2.69), 6.90 (d, 1 H, J=2.74), 3.97 (br s, 2 H, NH$_2$); $^{13}$C NMR (75 MHz, CDCl$_3$) δ146.8, 144.5, 143.5, 133.7, 130.6, 129.7, 121.5, 121.4, 107.4; MS (CI/NH$_3$) 145.

The rearrangement product was also isolated from the column as a brown solid (250, 1.21 mmol, 32.7% yield): mp 162–165° C.; $^1$H NMR (300 MHz, CDCl$_3$) δ9.02 (br s, 1 H, N—H), 8.82 (dd, 1 H, J=4.35, 1.66 Hz), 8.46 (d, 1 H, J=2.51), 8.14–8.10 (m, 1 H), 8.06 (d, 1 H, J=9.12 Hz) 7.60 (dd, 1 H, J=9.0, 2.49), 7.38 (dd, 1 H, J=8.35, 4.33), 3.20 (br s, 1 H, OH), 1.62 (s, 6 H, C(CH$_3$)$_2$) $^{13}$C NMR (75 MHz, CDCl$_3$) δ174.7, 149.2, 145.4, 136.0, 135.5, 130.0, 128.8, 123.2, 121.6, 115.7, 74.3, 28.0; MS (CI/NH$_3$) 231; IR (KBr pellet) 1674 (CO), 3308 (OH).

EXAMPLE 6

4-hydroxyquinolne

Preparation of 4-aminoquinoline

To a solution of 4-hydroxyquinoline (537 mg, 3.70 mmol) in dioxane (20 mL) was added NaH (Aldrich, dry, 300 mg, 12.2 mmol) and Cs$_2$CO$_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried (Na$_2$SO$_4$), and concentrated to about 3 g of material. The brown oil was distilled by Kugelrohr to remove residual NMP and DMPU, then chromatographed on silica (200 mL, 4 cm diam. column), eluting with 9:1 CHCl$_3$/MeOH then 7:3 CHCl$_3$/MeOH to obtain 4-aminoquinoline as an off-white solid (140 mg, 0.97 mmol, 26.2% yield).: mp 146–148° C. (lit. 154–155° C., Suzuki, Y., J. Pharm. Soc. Jpn., 1961, 81, 1146); $^1$H NMR (300 MHz, CDCl$_3$) δ8.30 (d, 1 H, J=6.20 Hz), 8.22 (d, 1 H, J=8.39 Hz), 7.78 (d, 1 H, J=8.89 Hz), 7.68–7.62 (m, 1 H), 7.49–7.38 (m, 3 H), 6.59 (d, 1 H, J=5.99 Hz); MS (EI) 144.

EXAMPLE 7

4-Hydroxypyridine

Preparation of 4-aminopyridine

To a solution of 4-hydroxypyridine (352 mg, 3.70 mmol) in dioxane (20 mL) was added NaH (Aldrich, dry, 300 mg, 12.2 mmol) and Cs$_2$CO$_3$ (4.00 g, 12.2 mmol). The resulting mixture was stirred at room temperature for about 30 minutes, then 2-bromo-2-methyl-propanamide (2.03 g, 12.2 mmol) was added and the resulting mixture was stirred at reflux for 16 h. After the reflux period, NMP (20 mL), DMPU (2 mL), and NaH (Aldrich, dry, 100 mg, 4.07 mmol) were added. The resulting mixture was stirred at 150° C. for 72 h. The reaction was cooled to room temp., and partitioned between water (50 mL) and EtOAc (100 mL). The aqueous layer was extracted with EtOAc (100 mL) and the combined organics washed with water (2×50 mL), dried (Na$_2$SO$_4$), and concentrated to about 3 g of material. The brown oil was distilled by Kugelrohr to remove most of the residual NMP and DMPU. At this point there was evidence of 4-aminopyridine in the crude NMR: $^1$H NMR (300 MHz, CDCl$_3$) δ8.2 (d, 2 H), 6.6 (d, 2 H) as well as peaks characteristic of NMP and DMPU.

We claim:

1. A process of converting a hydroxy heteroaromatic compound to an heteroaromatic arylamine, comprising the steps of:
   (1) treating a salt of a hydroxy heteroaromatic compound with an alkylating agent; and
   (2) treating the reaction mixture with a Smiles solvent system and raising the temperature of the reaction mixture.

2. The process according to claim 1, wherein the alkaline solvent system comprises a strong base, an ethereal solvent and a large alkaline metal cation.

3. The process according to claim 2, wherein the strong base is selected from the group consisting of sodium hydride, potassium hydride lithium hydride, lithium bis-trimethylsilyl amide, sodium bis-trimethylsilyl amide, potassium bis-trimethylsilyl amide, n-butyllithium, sec-butyllithium, iso-butyllithium, tert-butyllithium and mixtures thereof.

4. The process according to claim 3, wherein the strong base is selected from the group consisting of sodium hydride, potassium hydride, lithium hydride and mixtures thereof.

5. The process according to claim 4, wherein the strong base is sodium hydride.

6. The process according to claim 2, wherein the ethereal solvent is selected from the group consisting of 1,4-dioxane, 1,3-dioxane, tetrahydrofuran, dimethoxyethane, 2-methoxyethyl ether, propyl ether, isopropyl ether, n-butyl ether, sec-butyl ether, tert-butyl ether, n-butylmethyl ether, tert-butylmethyl ether, n-butylethyl ether, sec-butylethyl ether, tert-butylethyl ether, n-butylpropyl ether, sec-butylpropyl ether, tert-butylpropyl ether and mixtures thereof.

7. The process according to claim 6, wherein the ethereal solvent is selected from the group consisting of 1,4-dioxane, 1,3-dioxane, tetrahydrofuran, and dimethoxyethane and mixtures thereof.

8. The process according to claim 7, wherein the ethereal solvent is selected from he group consisting of 1,4-dioxane, 1,3-dioxane and mixtures thereof.

9. The process according to claim 1, wherein the large alkaline metal cation is in the form of an inorganic cesium compound.

10. The process according to claim 9, wherein the inorganic cesium compound is selected from the group consisting of cesium carbonate, cesium acetate, cesium bicarbonate, cesium bromide, cesium chloride, cesium fluoride, cesium iodide and mixtures thereof.

11. The process according to claim 10, wherein the inorganic cesium compound is cesium carbonate.

12. The process according to claim 1, wherein the alkylating agent is selected from the group consisting of a secondary haloalkylamide and a tertiary haloalkylamide.

13. The process according to claim 12, wherein the alkylating agent is a tertiary haloalkylamide.

14. The process according to claim 13, wherein the tertiary haloalkylamide is selected from the group consisting of 2-bromo-2-methylpropanamide and 2-bromo-2-ethylbutanamide and mixtures thereof.

15. The process according to claim 14, wherein the alkylating agent is 2-bromo-2-methylpropanamide.

16. A process for converting a hydroxy heteroaromatic compound to an heteroaromatic arylamine, comprising the steps of:

(1) treating the reaction mixture comprising an alkylating solvent system and the hydroxy heteroaromatic compound to form a salt;

(2) treating the reaction mixture with an alkylating agent; and (3) treating the reaction mixture with a Smiles solvent system and raising the temperature of the reaction mixture.

17. The process according to claim 16, wherein the Smiles solvent system comprises an amide solvent, an anion-coordinating agent and a strong base.

18. The process according to claim 17, wherein the amide solvent is selected from the group consisting of 1-methyl-2-pyrrolidinone, dimethylformamide, dimethylacetamide, and mixtures thereof.

19. The process according to claim 18, wherein the amide solvent is 1-methyl-2-pyrrolidinone.

20. The process according to claim 16, wherein the anion-coordinating agent is selected from the group consisting of 1,3-dimethyltetrahydropyrimidin-2(1H)-one, hexamethylphosphoric triamide and a mixture thereof.

21. The process according to claim 17, wherein the anion-coordinating agent is 1,3-dimethyltetrahydropyrimidin-2(1H)-one.

22. The process according to claim 16, wherein the temperature of the reaction mixture is between about 65° C. to about 250° C.

23. The process according to claim 22, wherein the reaction temperature is between about 125° C. to about 175° C.

24. The process according to claim 16, wherein the alkylating solvent system comprises;

an ethereal solvent selected from the group consisting of 1,4-dioxane, 1,3-dioxane or mixtures thereof;

a large alkali metal cation in the form of cesium carbonate; and a strong base in the form of sodium hydride.

25. The process according to claim 24, wherein alkylating agent is 2-bromo-2-methylpropoanamide.

26. The process according to claim 25, wherein the Smiles solvent system comprises;

an amide solvent in the form of 1-methyl-2-pyrrolidinone;

an anion-coordinating agent in the form of 1,3-dimthyltetrahydroppyrimidin-2(1H)-one; and a strong base in the form of sodium hydride.

* * * * *